United States Patent
Kobayashi (10) Patent No.: US 10,545,098 B2
(45) Date of Patent: Jan. 28, 2020

(54) FOREIGN SUBSTANCE INSPECTION APPARATUS, PROCESSING APPARATUS, AND METHOD OF MANUFACTURING ARTICLE

(71) Applicant: CANON KABUSHIKI KAISHA, Tokyo (JP)

(72) Inventor: Kenichi Kobayashi, Utsunomiya (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 16/354,305

(22) Filed: Mar. 15, 2019

(65) Prior Publication Data
US 2019/0293570 A1 Sep. 26, 2019

(30) Foreign Application Priority Data

Mar. 20, 2018 (JP) ................................. 2018-052919

(51) Int. Cl.
*G01N 21/95* (2006.01)
*H01L 21/68* (2006.01)
(Continued)

(52) U.S. Cl.
CPC ..... *G01N 21/9501* (2013.01); *G01B 11/0608* (2013.01); *G01N 21/47* (2013.01);
(Continued)

(58) Field of Classification Search
CPC ...... G01N 21/94; G01N 21/47; G01N 21/885; G01N 21/9501; G01N 21/95607;
(Continued)

(56) References Cited

U.S. PATENT DOCUMENTS

2001/0048761 A1* 12/2001 Hamamatsu ....... G01N 21/8851
382/149
2007/0268484 A1* 11/2007 Matsui ................... G01N 21/47
356/237.3
(Continued)

FOREIGN PATENT DOCUMENTS

JP   H10019792 A   1/1998
JP   H11201743 A   7/1999
(Continued)

*Primary Examiner* — Hoa Q Pham
(74) *Attorney, Agent, or Firm* — Rossi, Kimms & McDowell LLP (57) ABSTRACT

A foreign substance inspection apparatus performs foreign substance detection processing of detecting a foreign substance present on a surface of a substrate. The apparatus includes a detector that includes a projector configured to project light onto the surface and an optical receiver configured to receive scattered light from the surface, a scanning mechanism configured to scan a position on the surface onto which the light is projected by the projector, and a controller configured to control the foreign substance detection processing so that detection of the foreign substance is performed on a detection region which is a region excluding, from the surface, an exclusion region where a step is present thereon, wherein the controller controls the projection by the projector so that light is not projected to the step.

14 Claims, 10 Drawing Sheets

(51) Int. Cl.
*G01N 21/956* (2006.01)
*G01B 11/06* (2006.01)
*G01N 21/47* (2006.01)

(52) U.S. Cl.
CPC ..... *G01N 21/95607* (2013.01); *H01L 21/681* (2013.01); *G01N 2021/95615* (2013.01)

(58) Field of Classification Search
CPC ... G01N 2021/95615; G01N 2223/646; G01N 23/18; G01N 2201/1053; G01B 11/0608; H01L 21/681
USPC .................. 356/237.1–237.5, 338, 600
See application file for complete search history.

(56) References Cited

U.S. PATENT DOCUMENTS

| | | | | |
|---|---|---|---|---|
| 2011/0051130 A1* | 3/2011 | Kawahara | .............. | G01N 21/94 356/237.3 |
| 2012/0044505 A1* | 2/2012 | Matsui | ............... | G01N 21/9501 356/612 |
| 2015/0003722 A1* | 1/2015 | Otani | ................. | G02B 21/0004 382/149 |

FOREIGN PATENT DOCUMENTS

| | | | |
|---|---|---|---|
| JP | 2011141195 A | 7/2011 |
| JP | 2012159513 A | 8/2012 |
| WO | 2007011630 A2 | 1/2007 |

\* cited by examiner

FOREIGN SUBSTANCE INSPECTION APPARATUS, PROCESSING APPARATUS, AND METHOD OF MANUFACTURING ARTICLE

BACKGROUND OF THE INVENTION

Field of the Invention

The present invention relates to a foreign substance inspection apparatus, a processing apparatus, and a method of manufacturing an article.

Description of the Related Art

An article that has a very fine structure such as a semiconductor device or the like can be manufactured by using a lithography apparatus such as a projection exposure apparatus and an imprint apparatus. In such a lithography apparatus, if a foreign substance is present on a substrate, it may cause a defect in the article to be manufactured. In addition, since an imprint material will be formed by bringing a mold into contact with the imprint material on a substrate, a foreign substance present on the substrate can damage the mold or reduce the lifespan of the mold.

Hence, a foreign substance inspection apparatus that detects a foreign substance on a substrate can be used. A foreign substance inspection apparatus will detect a foreign substance by irradiating a substrate with oblique incident light and causing an optical receiver to receive the scattered light from the foreign substance. For example, a very highly sensitive optical receiver, for example, a photomultiplier tube or the like can be used to detect a microscopic foreign substance of, for example, about several tens nanometers. In a photomultiplier tube, after electrons generated in a photocathode by the light incidence are accelerated by a high voltage, the electrons are made to collide with a plurality of stages of dynodes which are configured to generate secondary electrons. A current that has been accumulated until it has passed the dynode of the last stage is collected in an anode as an amplified signal. Although the photomultiplier tube is capable of detecting a very weak beam of light, it becomes incapable of detecting a foreign substance when a strong light beam reflected by the structure of the substrate enters the photomultiplier tube because the output of the photomultiplier tube will be saturated for a corresponding period of time. Furthermore, in a case in which an anode current which is equal to or more than the rating flows, there is a possibility that the photomultiplier tube will receive irreparable damage.

Japanese Patent Laid-Open No. 10-19792 discloses a surface foreign substance inspection apparatus that inspects the entire region (including the edge) of the surface of a substrate. When reciprocally scanning an inspection target object with a light beam, the surface foreign substrate inspection apparatus turns off a light source when a scan (the first half of the scan) is being performed from the outer side of the target object to the target object and turns on the light source and receives scattered light when a scan (the second half of the scan) is being performed from the target object to the outer side of the target object. Although a strong scattered light beam will be generated when a light beam hits the edge of the target object in the second half of the scan and a photoelectric converter will not normally operate in the subsequent corresponding period, this is not a problem since the first half of the next scan operation will follow and the light source will be turned off and the scattered light will not be detected.

Since the surface foreign substance inspection apparatus disclosed in Japanese Patent Laid-Open No. 10-19792 is an apparatus that inspects the surface of a substrate including the edge of the surface, the edge of the substrate is also irradiated with light. Hence, the technical concept disclosed in Japanese Patent Laid-Open No. 10-19792 does not try to prevent the light from hitting the edge of the substrate. In addition, the surface foreign substance inspection apparatus disclosed in Japanese Patent Laid-Open No. 10-19792 is inefficient in that it does not execute foreign substance detection in half of the scanning period.

SUMMARY OF THE INVENTION

The present invention provides a technique advantageous in efficiently performing foreign substance inspection while solving the problem of signal saturation in an optical receiver.

One of aspects of the present invention provides a foreign substance inspection apparatus that performs foreign substance detection processing of detecting a foreign substance present on a surface of a substrate, comprising: a detector that includes a projector configured to project light onto the surface and an optical receiver configured to receive scattered light from the surface; a scanning mechanism configured to scan a position on the surface onto which the light is projected by the projector; and a controller configured to control the foreign substance detection processing so that detection of the foreign substance is performed on a detection region which is a region excluding, from the surface, an exclusion region where a step is present thereon, wherein the controller controls the projection by the projector so that light is not projected to the step.

Further features of the present invention will become apparent from the following description of exemplary embodiments with reference to the attached drawings.

DESCRIPTION OF THE EMBODIMENTS

An exemplary embodiment of the present invention will be described hereinafter with reference to the accompanying drawings.

Figure 1:
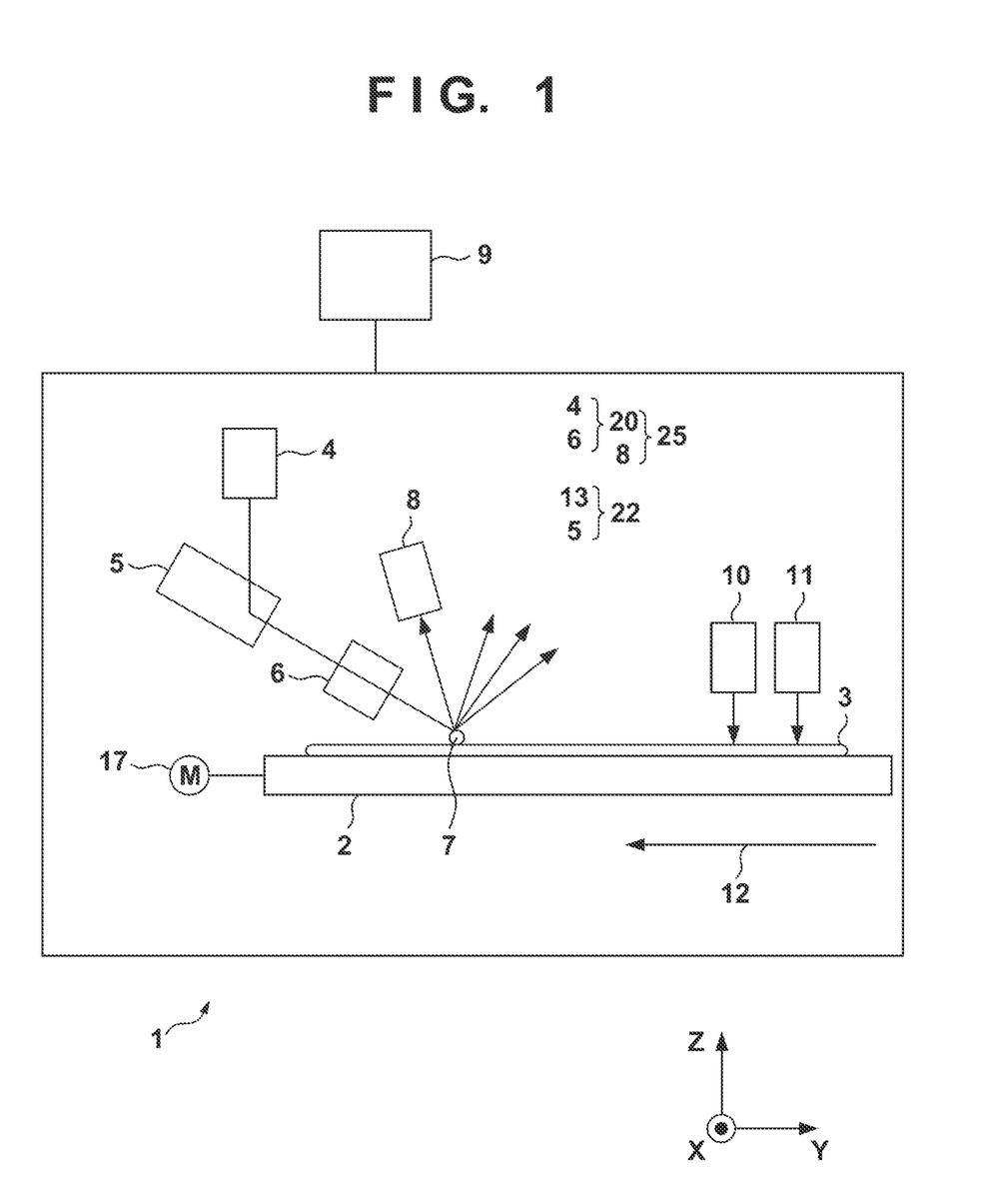
FIG. 1 is a side view showing an example of the arrangement of a foreign inspection apparatus according to an embodiment of the present invention.
Figure 2:
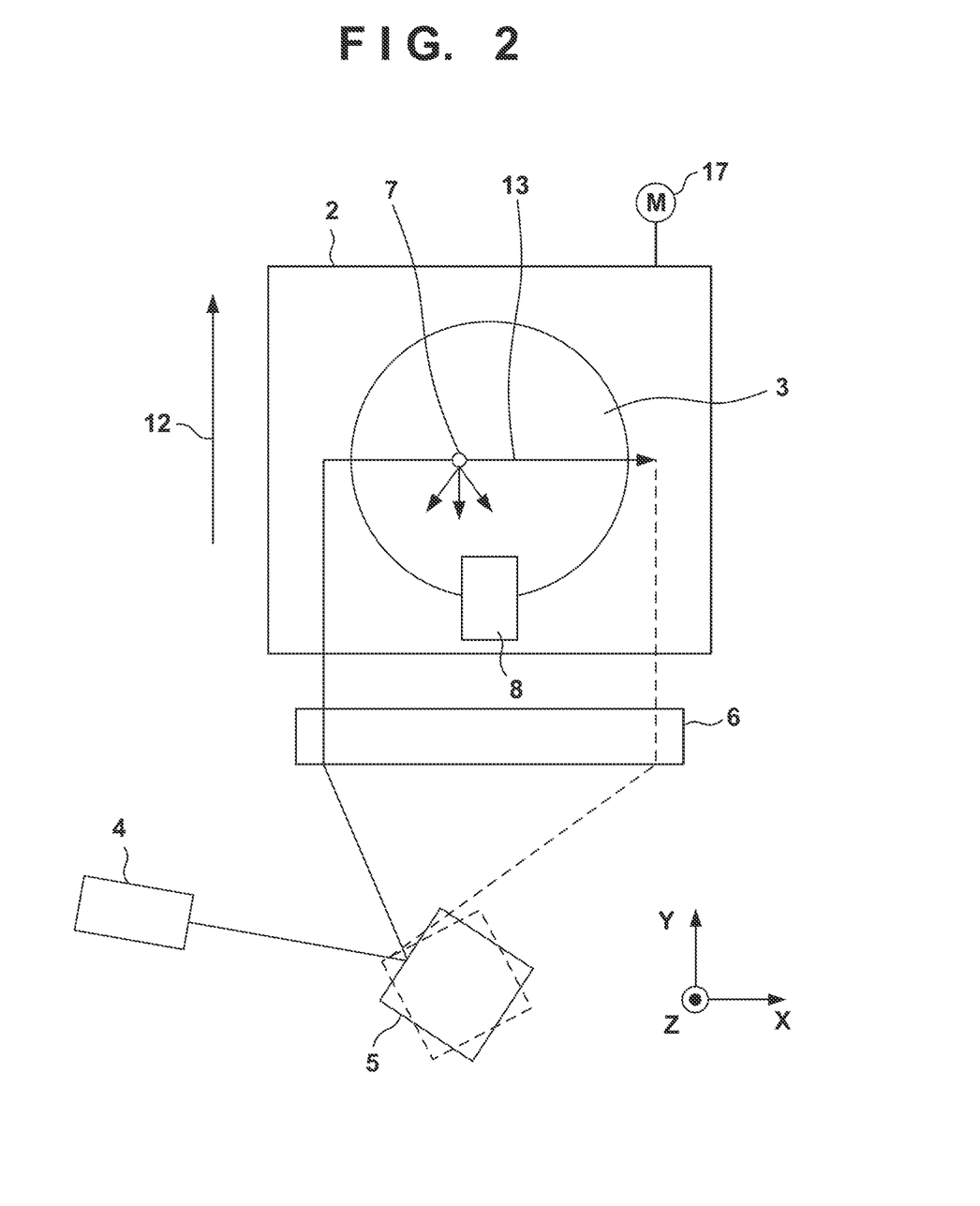
FIG. 2 is a plan view showing an example of the arrangement of the foreign inspection apparatus according to the embodiment of the present invention.

FIGS. 1 and 2 show an example of the arrangement of a foreign substance inspection apparatus 1 according to an embodiment of the present invention. FIG. 1 is a side view, and FIG. 2 is a plan view. An arrangement of the foreign substance inspection apparatus 1 will be described hereinafter in accordance with an XYZ coordinate system in which a plane parallel to the surface of a substrate 3 is set as an X-Y plane. Typically, the X-Y plane is a horizontal plane, and a Z-axis corresponds to a vertical plane.

The foreign substance inspection apparatus 1 is configured to perform foreign substance detection processing to detect a foreign substance 7 present on the surface of the substrate 3. The foreign substance inspection apparatus 1 can include a detector 25, a scanning mechanism 22, and a controller 9. The detector 25 can include a projector 20 that projects light onto the surface of the substrate 3, and an optical receiver 8 that receives scattered light from the surface of the substrate 3. The scanning mechanism 22 scans a position (light incident position on the substrate 3) on the surface of the substrate 3 onto which the projector 20 projects light.

The projector 20 can include, for example, a light source 4 and a projection optical system 6. The light source 4 generates light which is to be projected onto the surface of the substrate 3. The light source 4 can include, for example, a laser light source. In a case in which the foreign substance inspection apparatus 1 is to be used as an apparatus that checks the surface of the substrate 3 which has been applied with a photosensitive material, a wavelength that will not photosensitize the photosensitive material will be used as the wavelength of light to be generated by the light source 4. For example, light used by an imprint apparatus to cure a photosensitive material (imprint material) can be UV light. Hence, in a case in which the foreign substance inspection apparatus 1 is to be incorporated in an imprint apparatus or in a case in which the foreign substance inspection apparatus is to be used for the imprint apparatus, the wavelength of light to be generated by the light source 4 can be equal to or more than 400 nm. It is preferable for the light source 4 to be arranged so that the intensity of light to be generated can be changed in accordance with a process condition (for example, the reflectance of the surface of the substrate 3 with respect to the wavelength of the light generated by the light source 4) that is to be applied. It is possible to perform ON/OFF control at a frequency equal to or more than 100 MHz by using a semiconductor laser as the light source 4. The projection optical system 6 can include, for example, an ID lens. The optical receiver 8 can include, for example, a photomultiplier tube.

The scanning mechanism 22 can include, for example, a scanning mechanism 22, a polygon mirror unit (scanning optical system) 5, and a stage driving mechanism (stage scanning mechanism) 17. The polygon mirror unit 5 includes a polygon mirror and scans light by rotating the polygon mirror at a constant arbitrary speed. The stage driving mechanism 17 drives (scans), in at least a Y-axis direction, a stage (substrate holding device) 2 which holds the substrate 3. The stage driving mechanism 17 may further drive the stage 2 in another direction, for example, an X-axis direction and/or in a direction related to the rotation about the Z-axis. The scanning mechanism 22 performs scanning related to the X-axis direction by using the polygon mirror unit 5 and performs scanning related to the Y-axis direction by using the stage driving mechanism 17. However, both scanning operations in the X-axis direction and the Y-axis direction may be performed by an optical system including the polygon mirror unit 5 or may be performed by the stage driving mechanism 17.

Light emitted from the light source 4 irradiates the polygon mirror of the polygon mirror unit 5 and is reflected by the polygon mirror. Since the polygon mirror is required to be rotated, for example, at a speed of 10,000 rpm to 30,000 rpm, an air bearing which has superior durability can be used as the bearing to support the polygon mirror. The light reflected by the polygon mirror can be projected onto the substrate 3 via the projection optical system 6. As a result, the constant rotational movement of the polygon mirror can be converted into a constant linear movement of a spot that moves on the focal plane of the substrate 3. In addition, a telecentric-type lens that can emit light vertically onto the focal plane can be used as the ID lens of the projection optical system 6. In FIG. 2, a light scanning direction 13 indicates the scanning direction and its locus that have been converted by the constant linear movement. Also, in FIG. 2, a stage scanning direction 12 indicates the scanning direction and its locus of the stage 2. The light scanning direction 13 is perpendicular to the stage scanning direction 12.

The foreign substance 7 that adheres to the surface of the substrate 3 can be, for example, a particle having a minimum grain size which is equal to or more than several tens of nanometers. When the projector 20 irradiates the foreign substance with light, scattered light is generated from the foreign substance 7. The optical receiver 8 can be arranged so as to detect the reflection from the rear of the foreign substance 7 or detect the reflection from the side of the foreign substance 7.

The controller 9 can control the positioning of the stage 2 (control the stage driving mechanism 17), control ON/OFF of the light source 4, and control the polygon mirror unit 5. The controller 9 can also perform digital signal processing after analog electrical signals continuously output from the optical receiver 8 have been converted into digital signals. The digital signal processing can include, for example, processing to obtain the position of the center of gravity of the light intensity signal of a Gaussian distribution that has been obtained by the scattered light from the foreign substance 7. The digital signal processing can also include processing to calculate the coordinates of each foreign substance corresponding to the center coordinates (0, 0) of the substrate 3 based on the position of the center of gravity, the number of light scanning operations performed by the polygon mirror unit 5 corresponding to the position of the stage 2, and the number of data sampling operations from light scanning start position. The number of light scanning operations corresponds to a position in the Y-axis direction, the number of data sampling operations from the light scanning start position corresponds to a position in the X-axis direction. The digital signal processing also can include processing to obtain the grain size of the foreign substance 7 from the peak value and width of the obtained intensity distribution.

Figure 3:
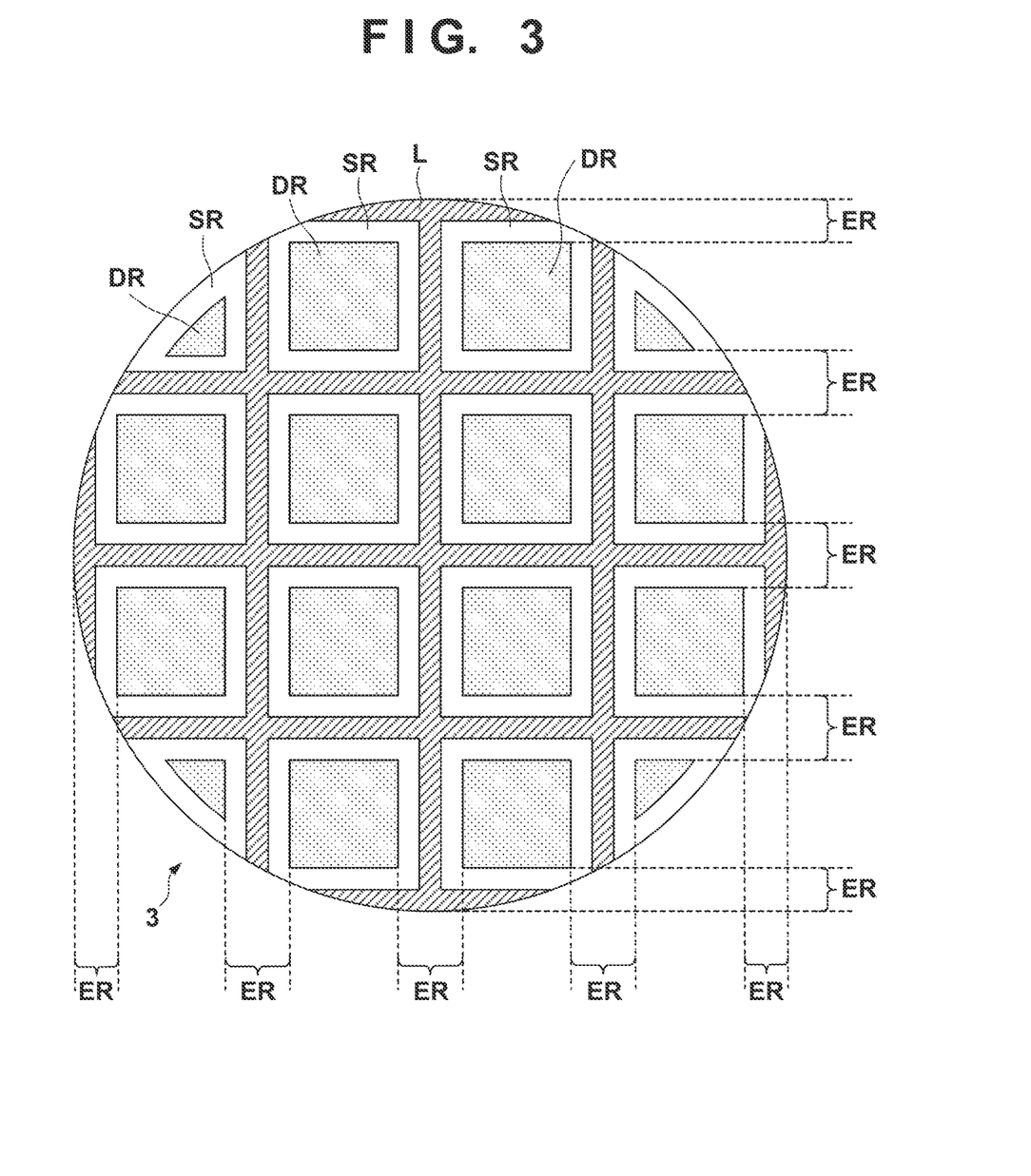
FIG. 3 is a schematic view showing an example of the arrangement of a substrate.

FIG. 3 shows a schematic example of the arrangement of the substrate 3. The substrate 3 can include a plurality of regions SR divided by scribe lines L. The substrate 3 has steps in its periphery including its edge. The substrate 3 also can include steps (for example, steps between the scribe lines L and the shot regions SR) formed by the scribe lines L. In one example, each region SR can be a shot region. Alternatively, in a case in which the shot region includes a plurality of chip regions, each region SR can be a chip region. The chip region is a region that is to be cut out by dicing and made into a chip such as a semiconductor chip. Steps as those described above can receive the light from the projector 20 and cause intensely reflected light to enter the optical receiver 8. The controller 9 can control the foreign substance detection processing so that detection of the foreign substance is performed on each detection region DR which is a region excluding, from the surface of the substrate 3, each exclusion region ER in which a step is present thereon. In this case, a step is a structure that can cause intensely reflected light to enter the optical receiver 8 upon receiving the light from the projector 20, and the steps can be discriminated from very fine concave-convex portions which are a collection of features such as a line and space pattern and the like in the shot region. The controller 9 can control the projection operation of the projector 20 so the projector 20 will not project light onto the steps on the surface of the substrate 3. The controller 9 can be formed from, for example, a PLD (the abbreviation of a Programmable Logic Device) such as an FPGA (the abbreviation of a Field Programmable Gate Array), an ASIC (the abbreviation of an Application Specific Integrated Circuit), a general purpose computer embedded with a program, or a combination of all or some of these components.

The foreign substance inspection apparatus 1 can include a measurement device (alignment scope) 10 that measures the position of each alignment mark on the substrate 3. The foreign substance inspection apparatus 1 can also include a measurement device 11 that measures the height of the surface of the substrate 3. The measurement device 11 can include, for example, a non-contact sensor such as a reflection-type laser displacement meter that can measure a mirror surface.

Figure 4:
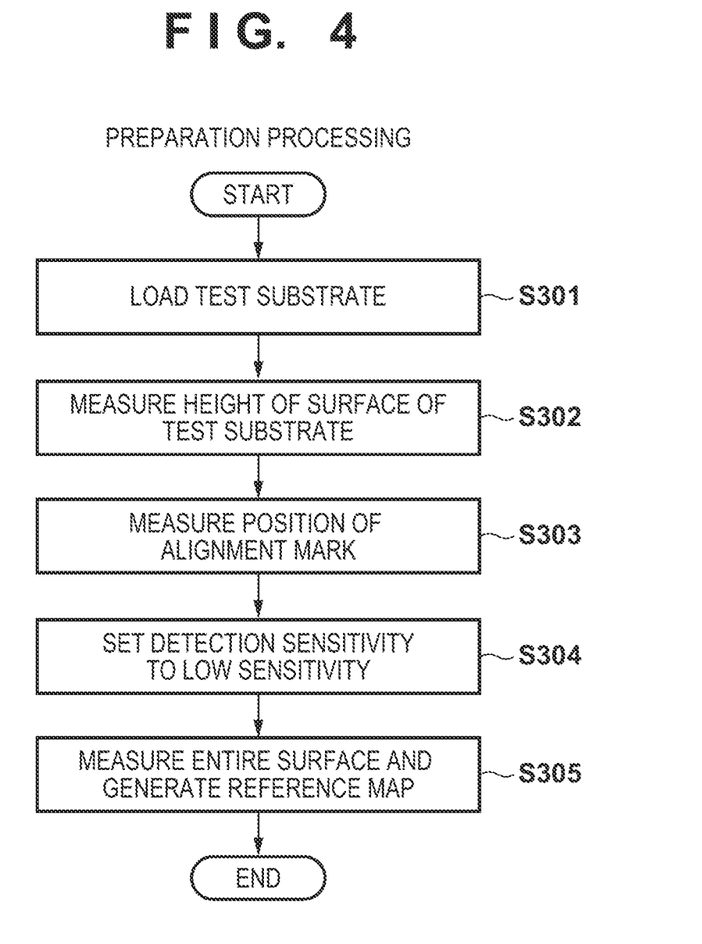
FIG. 4 is a flowchart showing an operation (preparation processing) of the foreign inspection apparatus according to the embodiment of the present invention.
Figure 5:
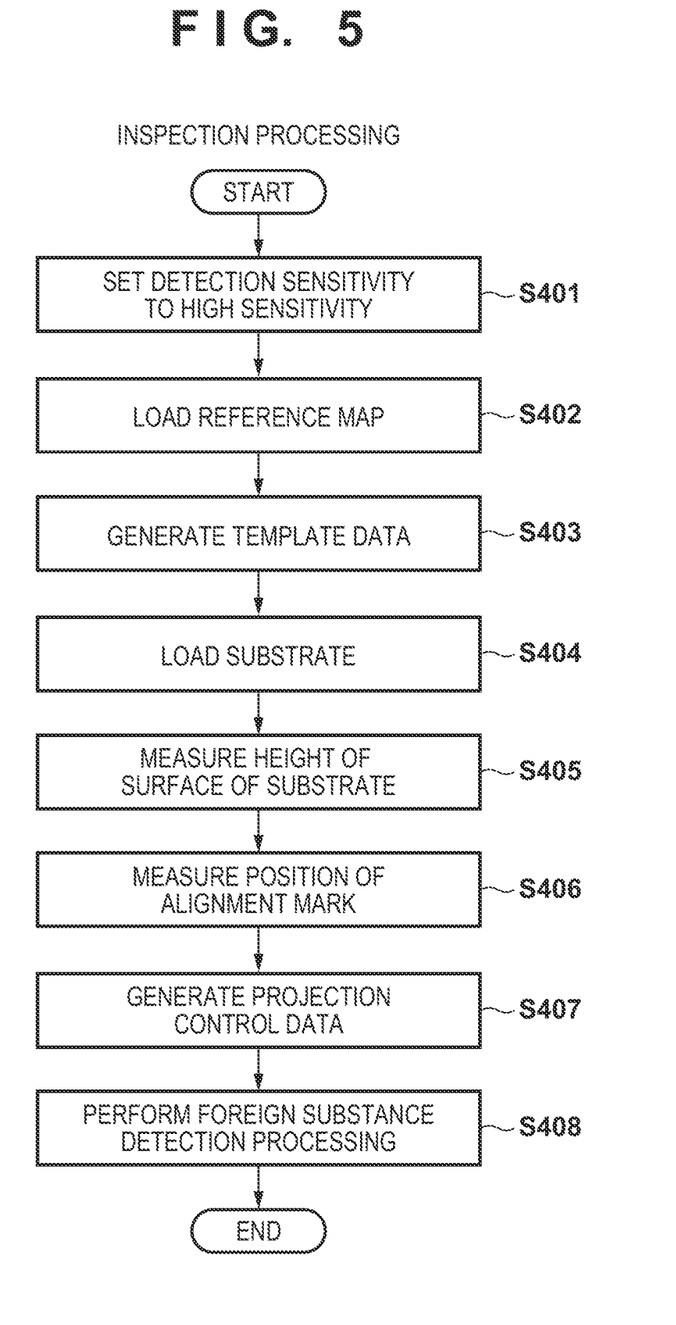
FIG. 5 is a flowchart showing an operation (inspection processing) of the foreign substance inspection apparatus according to the embodiment of the present invention.

The operation of the foreign substance inspection apparatus 1 will be exemplified with reference to FIGS. 4 and 5 hereinafter. The operation of the foreign substance inspection apparatus 1 can include the preparation processing illustrated in FIG. 4 and the inspection processing illustrated in FIG. 5. The controller 9 can control the preparation processing and the inspection processing.

The preparation processing will be described first with reference to FIG. 4. A reference map is generated in the preparation processing. A reference map is obtained by mapping the intensity of the reflected light (including the scattered light) from each position on the substrate 3 when the substrate 3 is scanned by the scanning mechanism 22. In step S301, a test substrate is placed on the stage 2. The test substrate may be the substrate 3 which is the inspection target in the inspection processing or may be another substrate which has a structure identical to the substrate 3.

In step S302, the measurement device 11 measures the height of the surface of the test substrate. In step S303, the measurement device 10 measures the position of the plurality of the alignment marks on the test substrate, and the controller 9 calculates a position $(X_{ref}, Y_{ref}, Qz_{ref})$ on the test substrate based on the measurement result. Assume that $X_{ref}$ and $Y_{ref}$ are a position in the X-axis direction and a position in the Y-axis direction, respectively, and the $Qz_{ref}$ is a rotation about the Z-axis. In step S304, the controller 9 sets the sensitivity of the detector 25 to low sensitivity so as to prevent the output of the optical receiver 8 from saturating on the entire surface including the edge of the test substrate.

The sensitivity setting of the detector 25 here may be made by setting the output intensity of the light source 4, by setting the sensitivity of the optical receiver 8, by setting the sensitivities of both the light source and the optical receiver, or by employing another method. For example, a method of arranging an ND filter on an optical path from the light source 4 to the test substrate and/or on an optical path from the test substrate to the optical receiver 8 may be employed as the other method.

In step S305, a measurement process is executed to measure the light, from the projector 20, which is reflected by the entire surface (including the edge) of the surface of the test substrate as the target. This measurement process can include a process of associating a position $(X_{ref}, Y_{ref})$ on the surface of the test substrate with a signal I obtained as an output from the optical receiver 8 while causing the scanning mechanism 22 to operate and causing the projector 20 to project light onto the surface of the test substrate, and storing the information of the associated position and the signal. The reference map, for example, can be formed as a set of a plurality of the data elements $(X_{ref}, Y_{ref},$ and I). This measurement process differs from the foreign substance detection processing performed in the inspection processing (to be described later) in the points that the detection sensitivity is set to low, the light source 4 is continuously maintained in an ON state (lit state), and the foreign substance detection is not performed based on the output from the optical receiver 8. However, other points are the same as those of the foreign substance detection processing.

The interval between each position (X, Y) to be measured can be determined in accordance with, for example, the light scanning speed of the polygon mirror unit 5, the speed at which the stage driving mechanism 17 scans the stage 2, and the frequency of the frequency modulation controllable by the light source 4. For example, in a case in which the light scanning speed of the polygon mirror unit 5 is 700 m/sec and the frequency of the frequency modulation by the light source 4 is 100 MHz (0.01 μsec), the minimum pitch in the X-axis direction can be 7 μm. In addition, in a case in which the speed at which the stage 2 is scanned is 20 mm/sec and the light scanning frequency is 1500 Hz, the minimum pitch in the Y-axis direction can be 13.3 μm. The reference map can be generated for each process (process ID).

The inspection processing will be described with reference to FIG. 5 hereinafter. First, in step S401, the controller 9 sets the detector 25 to high sensitivity (sensitivity at which foreign substance detection can be performed). The sensitivity of the detector 25 can be determined for each process (process ID). In step S402, the controller 9 loads the reference map generated by the preparation processing (FIG. 4) performed in correspondence with the process to be performed on the inspection target substrate 3. In step S403, the controller 9 executes a generation process of generating template data. The template data is data used to control the light projection by the projector 20 in accordance with the scanning performed by the scanning mechanism 22 so that light will be projected onto each detection region DR on the substrate 3. In this generation process, the controller 9 generates the template data based on the reference map (the signal stored in the measurement process) so the projector 20 will not project light to the steps (exclusion regions ER) of the substrate 3.

More specifically, the controller 9 converts the value of the signal I (the signal stored in the measurement process) on the reference map into a value (to be referred to as a conversion value hereinafter) CV of the sensitivity of the detector 25 to be used in the inspection processing (the foreign substance detection processing in step S408). For example, assuming that the sensitivity of the detector 25 in the preparation processing is S1 and the sensitivity of the detector 25 in the inspection processing (the foreign substance detection processing in step S408) is S2, the conversion value CV can be calculated by CV=I×S2/S1. Subsequently, the controller 9 can generate the template data so as to turn off the light source 4 in each position (X, Y) where the conversion value CV exceeds a threshold TH determined based on an allowed output value of the optical receiver 8 and turn on the light source 4 in each position (X, Y) where the conversion value CV does not exceed the threshold TH.

The template data can be formed by a set of data elements (X, Y, and E). Assume that the data element E can be ON/OFF data determined by setting "1" when the light source 4 is to be turned on and setting "0" when the light source 4 is to be turned off. The set of positions (X, Y) where the light source 4 is to be turned on forms each detection region DR, and the set of positions (X, Y) where the light source 4 is to be turned off forms each exclusion region ER. The allowed output value of the optical receiver 8 can be determined in accordance with the specifications of the optical receiver 8 so the output of the optical receiver 8 will not be saturated and the optical receiver 8 will not be damaged while typically ensuring a corresponding margin. In this example, the preparation processing illustrated in FIG. 4 and step S403 (generation process) of the inspection processing illustrated in FIG. 5 form the template data generation processing that generates template data. Step S403 (generation process) may be incorporated in the preparation processing instead of this example.

Since a foreign substance cannot be detected in each exclusion region ER, which is a set of the positions (X, Y) where the light source 4 will not be turned on, the exclusion region ER needs to be made as small as possible. Hence, the light scanning performed by the scanning mechanism 22 and (the exclusion regions ER and the detection regions DR of) the substrate 3 need to be aligned with high accuracy. On the other hand, the height of the surface of the substrate 3 can vary between the substrates 3. For example, consider a case in which the angle of incidence of the light projected by the projector 20 to the substrate 3 is 80° and the difference between the height of the surface of the test substrate and the height of the surface of the inspection target substrate 3 is 20 μm. In this case, the position of the light incident on the substrate 3 shifts across) 20/tan(10°=113.4 μm in the scanning direction (direction parallel to the Y-axis direction) of the stage 2 with respect to position of the light incident on the test substrate. In addition, in a case in which the substrate 3 is loaded to the stage 2 by a conveyance mechanism (not shown), the substrate 3 can be arranged with corresponding arrangement errors on the stage 2.

Thus, in step S405, the measurement device 11 measures the height of the surface of the substrate 3. In addition, in step S406, the measurement device 10 measures the positions of a plurality of alignment marks on the substrate 3, and the controller 9 calculates each position (X, Y, and Qz) on the substrate 3 based on the measurement result. In step S407, the controller 9 generates projection control data by correcting the template data, generated in step S403, based on the measurement result(s) obtained by the measurement device 11 and/or the measurement device 10. As described above, it becomes possible to set each exclusion region ER to be small by generating the projection control data by correcting the template data in the above-described manner. This allows foreign substance inspection to be performed by setting each wider region on the surface of the substrate 3 as the detection region DR. However, note that the processes of steps S405 to S407 are not required to be performed, and the template data generated in step S403 may be used directly as the projection control data.

In step S408, the controller 9 controls the foreign substance detection processing so that foreign substance detection will be performed on each target detection region DR obtained by excluding each exclusion region ER in which steps are present from the surface of the substrate 3. More specifically, the controller 9 detects each foreign substance on the surface of the substrate 3 by controlling the projection (ON/OFF of the light source 4) by the projector 20 based on the projection control data. That is, in the foreign substance detection processing, the controller 9 controls the projection operation by the projector 20 based on the projection control data so the projector 20 will not project light on the steps of the surface of the substrate 3.

Figure 6:
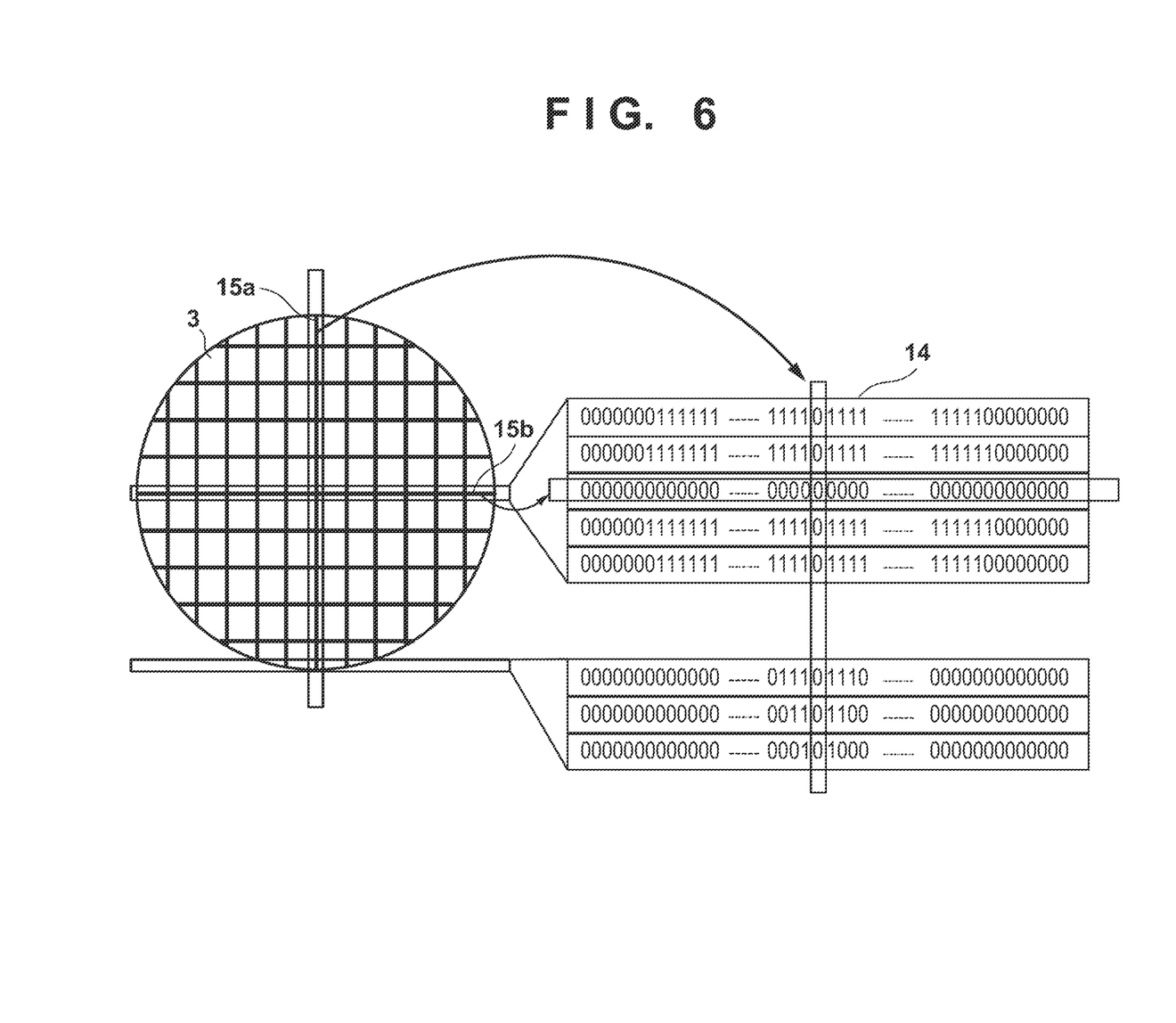
FIG. 6 is a schematic view of projection control data.

FIG. 6 schematically shows projection control data 14. The projection control data 14 is data obtained by dividing the entire surface of the substrate 3 into small regions at a pitch that will allow the light source 4 to be turned on or off and assigning ON/OFF data indicating, with respect to each small region, whether the light source 4 is to be turned on or off. The projection control data 14 is data that can have the same format as the aforementioned template data and can be formed by the set of data elements (X, Y, and E). X, Y are the coordinates of each small region, and E is the ON/OFF data.

In the projection control data 14 shown in FIG. 6, "0" and "1" are the ON/OFF data E, and each position in which "0" and "1" have been arranged schematically shows the coordinates (X, Y) of the small region. "1" indicates the time at which the light source 4 is to be turned on, and "0" indicates the time at which the light source 4 is to be turned off. In the projection control data 14 shown in FIG. 6, each line arranged in the horizontal direction is a line to be scanned by the polygon mirror unit 5. Also, the number of lines is the number of lines to be scanned by the stage driving mechanism 17. The substrate 3 can include each exclusion region where steps are present. In FIG. 6, reference numerals 15a and 15b indicate some of the line-shaped exclusion regions. The exclusion regions 15a and 15b can include scribe lines. In the projection control data 14 shown in FIG. 6, portions corresponding to the exclusion regions 15a and 15b are formed by "0", and this indicates that the light from the projector 20 will not be projected onto the exclusion regions 15a and 15b.

Although a reference map is generated and projection control data is generated based on the reference map in the example described above, the information indicating the positions of steps on the substrate 3 may be obtained based on the design information used for manufacturing an article such as a semiconductor device by processing the substrate 3. That is, the projection control data may be generated based on the design information.

A method of generating the project control data based on the template data and the measurement result obtained by the measurement device 10 will be exemplified in step S407 hereinafter. Arrangement errors (ΔX, ΔY, ΔQz) of the substrate 3, which is to be arranged on the stage 2 in step S404, can be expressed by using a position (X, Y, Qz) calculated in step S406 and a position $X_{ref}$, $Y_{ref}$, $Qz_{ref}$) calculated in step S303 in the manner of $$(\Delta X, \Delta Y, Qz) = (X - X_{ref}, Y - Y_{ref}, Q_z - Qz_{ref})$$

Thus, the projection control data can be obtained by shifting and rotating the template data by ΔX, ΔY, and ΔQz.

To achieve this, X and Y of the template data can be moved to X' and Y', respectively, in accordance with $$X' = \sqrt{X^2 + Y^2} \times \cos\left(\Delta Qz + \tan^{-1}\left(\frac{Y}{X}\right) - \Delta X\right) \quad (2)$$

$$Y' = \sqrt{X^2 + Y^2} \times \sin\left(\Delta Qz + \tan^{-1}\left(\frac{Y}{X}\right) - \Delta Y\right) \quad (3)$$

As a result, the arrangement errors of the substrate 3 can be scanned.

Figure 7:
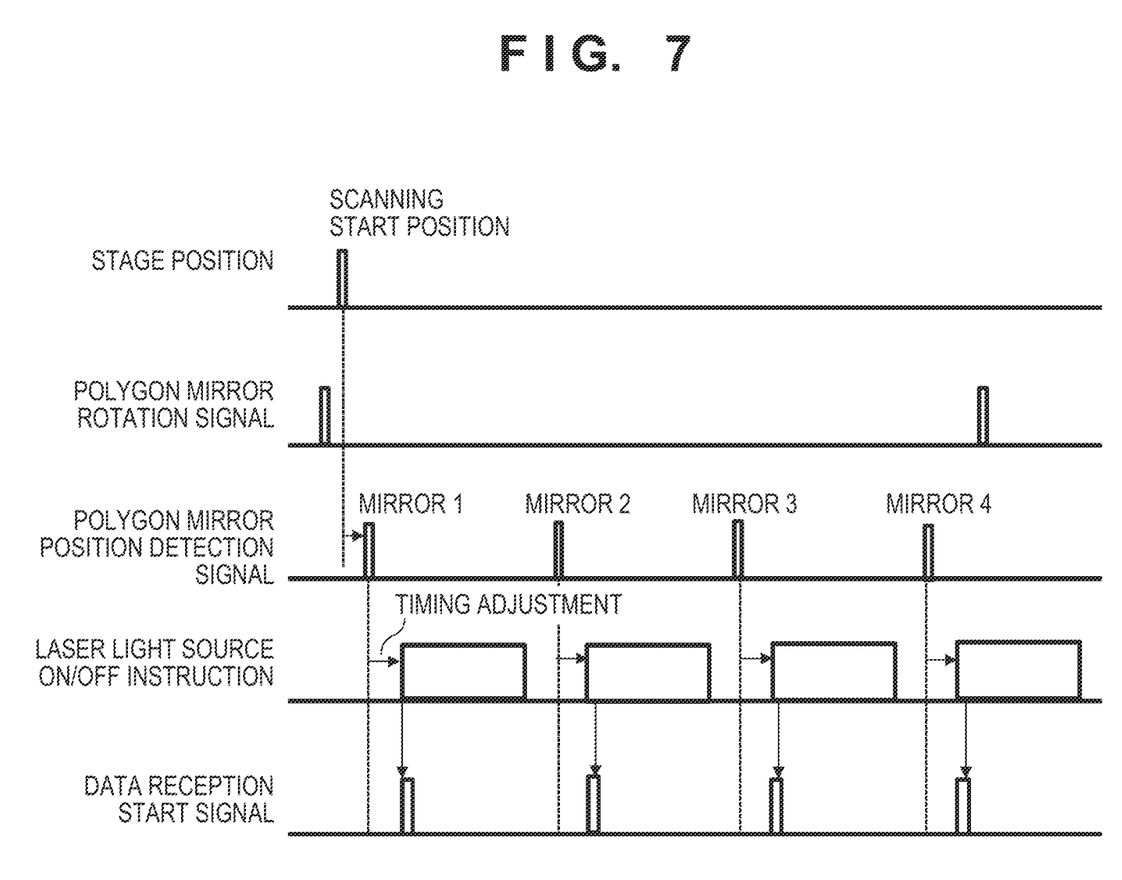
FIG. 7 is a timing chart showing an example of timing signals in the foreign substance inspection apparatus according to the embodiment.

FIG. 7 shows an example of timing signals in the foreign substance inspection apparatus 1. A "polygon mirror rotation signal" is a signal indicating the rotation angle of the polygon mirror of the polygon mirror unit 5, and one pulse is generated each time the polygon mirror rotates once. The "polygon mirror rotation signal" can be generated by using a Hall element or a rotary encoder provided on a rotation shaft of a motor configured to rotate the polygon mirror. Alternatively, the "polygon mirror rotation signal" can be generated by causing an optical sensor to detect a mark arranged on the upper surface or the like of the polygon mirror. A "polygon mirror position detection signal" can be generated by irradiating the edge surface of the polygon mirror with light generated by branching the light from the light source 4 by a half mirror or with light generated by another light source, and detecting the reflected light from the edge surface by a photodiode or the like. As a result, the specific position of the polygon mirror (for example, a four-faced mirror). The mirror number of the polygon mirror and the position of each mirror can be specified based on the "polygon mirror rotation signal" and the "polygon position detection signal".

After the stage 2 has reached the target speed and has shifted to a constant speed driving operation, a measurement operation can be started at the timing when the stage 2 has reached the measurement start position. The measurement start position can be determined based on an encoder signal used for positioning control of the stage 2. When the measurement operation is started, the ON/OFF control of the light source 4 based on the projection control data 14 of the first line can be started at a timing synchronized with the first pulse of the "polygon mirror position detection signal". Also, at this timing, a data reception signal for receiving continuous analog signals from the optical receiver 8 can be output. After the ON/OFF control of the light source 4 and the data reception from the optical receiver 8 with respect to the first line have been completed, the process shifts to a standby state for the next pulse of the "polygon mirror position detection signal". Subsequently, at the timing synchronized with the next pulse of the "polygon mirror position detection signal", the ON/OFF control of the light source 4 based on the projection control data 14 of the second line can be started. This kind of operation can be repeated for the set number of lines.

The light irradiation position on the substrate 3 at the timing synchronized with the pulse of the "polygon mirror position detection signal" can differ between the plurality of mirrors belonging to the polygon mirror. The irradiation variation can be caused by a process error of the mirrors. Since the variation between the mirrors can be detected by repeatedly measuring a specific foreign substance in a state in which the stage 2 stopped still, the projection control data 14 and the data reception start timing can be adjusted for each mirror so the irradiation position will be constant. The light scanning position, data reception, and the scanning position of the stage 2 can be synchronized accurately by executing timing adjustment for each mirror.

The position (X, Y, Qz) calculated in step S406 can be used for correcting the coordinates of each detected foreign substance. The controller 9 can, for example, convert the position (X, Y) of the detected foreign substance into a corrected position (X', Y') in accordance with $$X' = \sqrt{X^2 + Y^2} \times \cos\left(\Delta Qz + \tan^{-1}\left(\frac{Y}{X}\right) - \Delta X\right) \quad (4)$$

$$Y' = \sqrt{X^2 + Y^2} \times \sin\left(\Delta Qz + \tan^{-1}\left(\frac{Y}{X}\right) - \Delta Y\right) \quad (5)$$

As a result of the foreign substance with respect to the reference defined by each alignment mark can be specified accurately.

Figure 8:
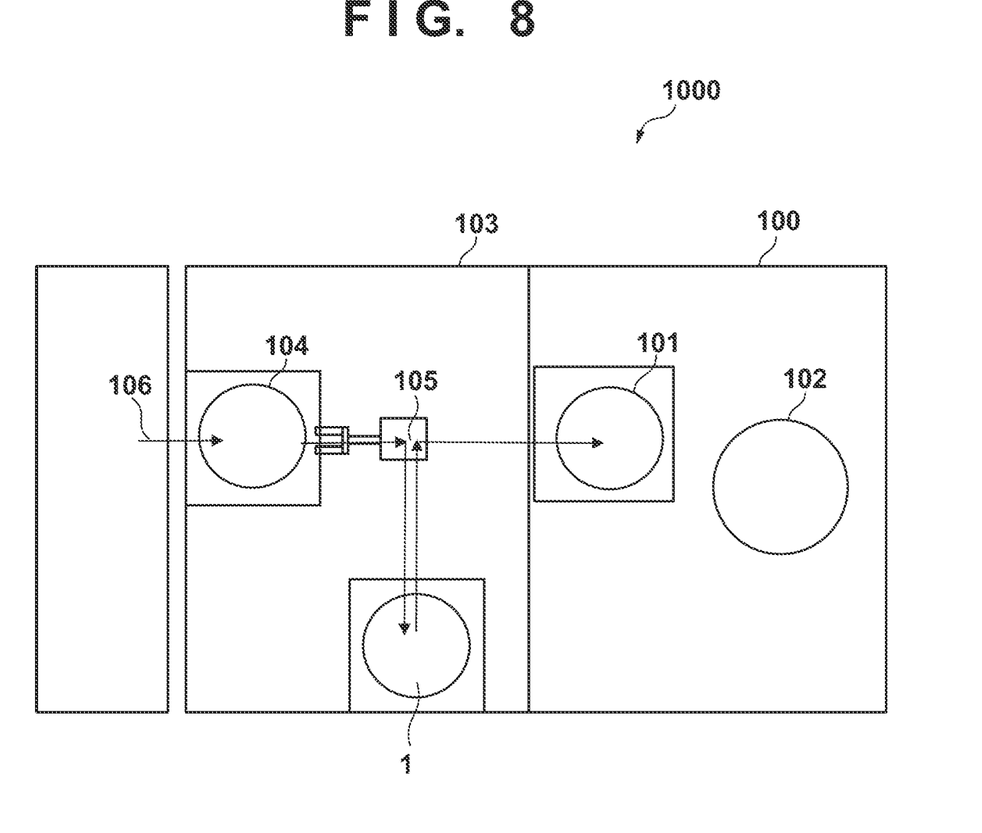
FIG. 8 is a view showing a processing apparatus according to the embodiment of the present invention.

FIG. 8 shows the arrangement of a processing apparatus 1000 according to an embodiment of the present invention. The processing apparatus 1000 can include the foreign substance inspection apparatus 1 and a forming apparatus 100. The forming apparatus 100 can be formed so as to perform forming processing to form a composition on the substrate 3 by using a mold. In one example, the forming apparatus 100 can be arranged as an imprint apparatus that forms a composition (imprint material) on the substrate 3 by using a mold with a pattern, in other words, the forming apparatus can be formed as an imprint apparatus that transfers the pattern of the mold to the composition on the substrate 3. An imprint apparatus can form a pattern formed from a cured composition on the substrate 3 by curing the composition in a state in which the mold and the composition on the substrate 3 are in contact with each other. In another example, the forming apparatus 100 can be arranged as a planarization apparatus that can planarize the composition on the substrate 3 by using a mold (a blank template) which has a flat surface portion without an uneven pattern. The planarization apparatus can form a film with a flat upper surface made of the cured composition by curing the composition in a state in which the planar portion of the mold is in contact with the composition on the substrate 3.

The processing apparatus 1000, or the forming apparatus 100 can include a positioning mechanism 101 configured to position the substrate 3 and a forming device 102 configured to cure the composition on the substrate by irradiating the composition with curing energy (for example, UV light) in a state in which the mold and the composition on the substrate 3 are in contact with each other.

The forming apparatus 100 can be connected to a conveyance chamber 103. The conveyance chamber 103 can be connected to an auxiliary mechanism 106 such as a coater/developer. The auxiliary mechanism 106 is an apparatus that arranges a composition on the substrate 3. The auxiliary mechanism 106 can supply the substrate 3 on which the composition is arranged to a station 104 in the conveyance chamber 103. A conveyance mechanism 105 can convey the substrate 3 supplied to the station 104 to the stage 2 of the foreign substance inspection apparatus 1. The foreign substance inspection apparatus 1 performs foreign substance detection processing to detect a foreign substance present on the surface of the substrate 3. A substrate in which the presence of a foreign substance cannot be determined by the foreign substance inspection apparatus 1 can be conveyed to the substrate positioning mechanism 101 of the forming apparatus 100 by the conveyance mechanism 105. On the other hand, a substrate in which the presence of a foreign substance has been determined by the foreign substance inspection apparatus 1 can be returned to the auxiliary mechanism 106 or discharged through a discharge port (not shown) by the conveyance mechanism 105.

Figure 9:
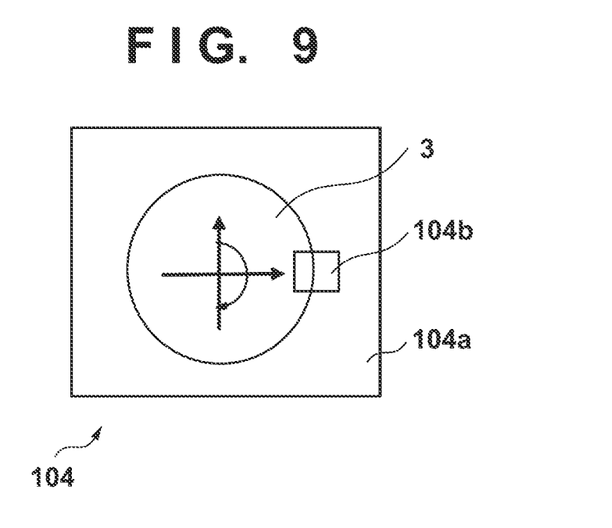
FIG. 9 is a view showing an example of the arrangement of a station.

FIG. 9 shows an example of the arrangement of the station 104. The station 104 can function as a measurement device that has a function of measuring errors related to the position and the rotation of the substrate 3 based on the outer shape of the substrate 3. The station 104 can include, for example, a driving mechanism 104a configured to drive the substrate 3 with respect to rotation about the X-axis, the Y-axis, and the Z-axis and a substrate edge detector 104b. The substrate edge detector 104b is configured to detect the edge position of the substrate 3 and can include, for example, a licensor. The orientation (notch position) of the substrate 3 and the outer shape of the substrate 3 can be obtained by causing the substrate edge detector 104b to detect the edge position of the substrate 3 while the substrate 3 is rotated by the driving mechanism 104a. In addition, the conveyance mechanism 105 can convey the substrate 3 with high positional accuracy by calculating the center position of the substrate 3 based on the outer shape of the substrate 3 and offsetting the position (X, Y, Qz) of the substrate 3 so the conveyance mechanism 105 can constantly receive the substrate 3 at the same position.

The errors related to the position and the rotation of the substrate 3, which have measured based on the outer shape of the substrate 3 by the station 104 that functions as a measurement device, can be used in step S407 to generate the projection control data 14, that is, to correct the template data. For example, in a case in which the outer shape of the test substrate for generating a reference map is used as a reference and the outer shape of the inspection target substrate 3 includes a region smaller than the reference, the projection control data 14 can be generated so the light will not be projected to this region. In contrast, the projection control data 14 will be generated so the light will be projected to a region of the outer shape which is larger than the reference. As a result, each exclusion region ER can be accurately determined without depending on the variation of the outer shape of the substrate 3. In this example, although the measurement of the outer shape of the substrate 3 is performed in the station 104, a function that rotates the stage 2 and a substrate edge detector that detects the edge of the substrate 3 rotated together with the stage 2 can be arranged.

The pattern of a cured product formed using the imprint apparatus is used permanently for at least some of various kinds of articles or temporarily when manufacturing various kinds of articles. The articles are an electric circuit element, an optical element, a MEMS, a recording element, a sensor, a mold, and the like. Examples of the electric circuit element are volatile and nonvolatile semiconductor memories such as a DRAM, a SRAM, a flash memory, and a MRAM and semiconductor elements such as an LSI, a CCD, an image sensor, and an FPGA. Examples of the optical element are a microlens, a light-guiding member, a waveguide, an antireflection film, diffraction grating, a light polarization element, a color filter, a light emitting element, a display, a solar battery, and the like. Examples of the MEMS are a DMD, a microchannel, an electromechanical transducer, and the like. Examples of the recording element are an optical disk such as a CD or DVD, a magnetic disk, a magnetooptical disk, a magnetic head, and the like. Examples of the sensor are a magnetic sensor, an optical sensor, a gyro sensor, and the like. Examples of the mold are molds for imprint.

The pattern of the cured product is directly used as the constituent member of at least some of the above-described articles or used temporarily as a resist mask. After etching or ion implantation is performed in the substrate processing step, the resist mask is removed.

Figure 10A:
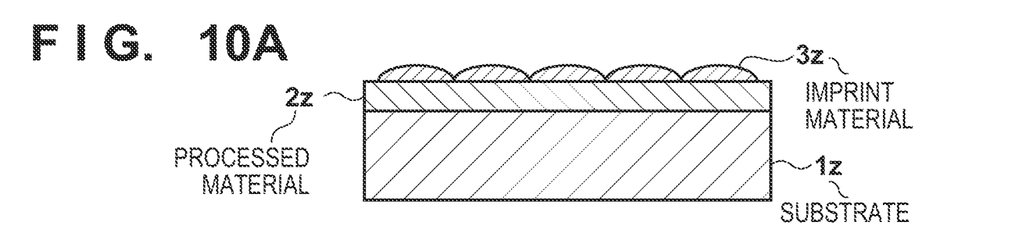
FIGS. 10A to 10F are views showing an example of a method of manufacturing an article.

An article manufacturing method of forming a pattern on a substrate by an imprint apparatus, processing the substrate on which the pattern has been formed, and manufacturing an article from the processed substrate will be described next. As shown in FIG. 10A, a substrate 1z such as a silicon wafer with a processed material 2z such as an insulator formed on the surface is prepared. Next, an imprint material 3z is applied to the surface of the processed material 2z by an inkjet method or the like. A state in which the imprint material 3z is applied as a plurality of droplets onto the substrate is shown here.

Figure 10B:
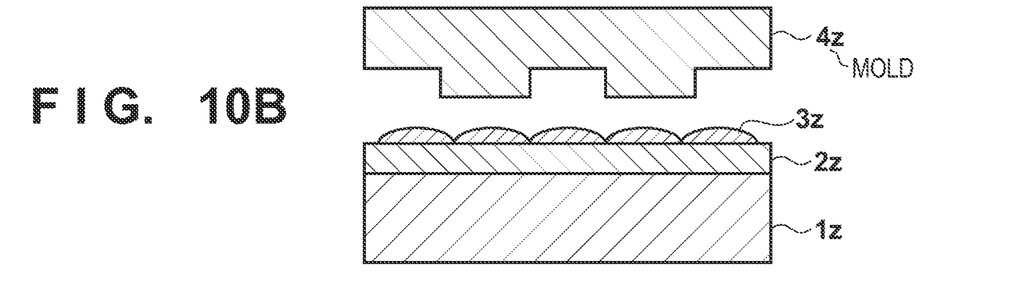
Figure 10C:
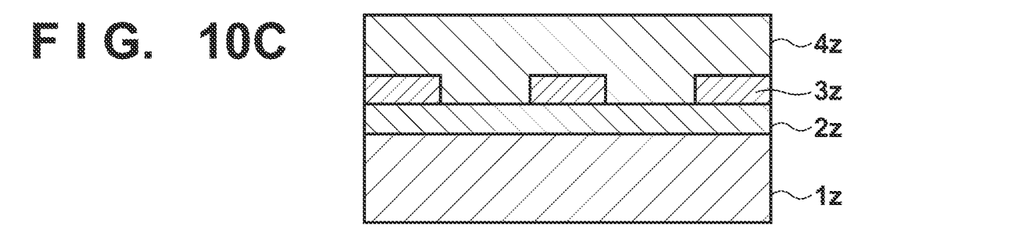

As shown in FIG. 10B, a side of a mold 4z for imprint with an uneven pattern is directed to and caused to face the imprint material 3z on the substrate. As shown in FIG. 10C, the substrate 1z to which the imprint material 3z is applied is brought into contact with the mold 4z, and a pressure is applied. The gap between the mold 4z and the processed material 2z is filled with the imprint material 3z. In this state, when the imprint material 3z is irradiated with enemy for curing via the mold 4z, the imprint material 3z is cured.

Figure 10D:
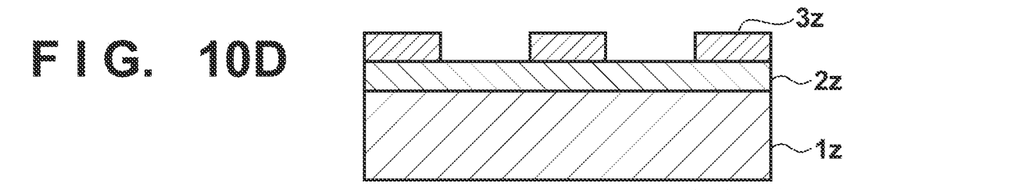

As shown in FIG. 10D, after the imprint material 3z is cured, the mold 4z is separated from the substrate 1z. Then, the pattern of the cured product of the imprint material 3z is formed on the substrate 1z. In the pattern of the cured product, the concave portion of the mold corresponds to the convex portion of the cured product, and the convex portion of the mold corresponds to the concave portion of the cured product. That is, the uneven pattern of the mold 4z is transferred to the imprint material 3z.

Figure 10E:
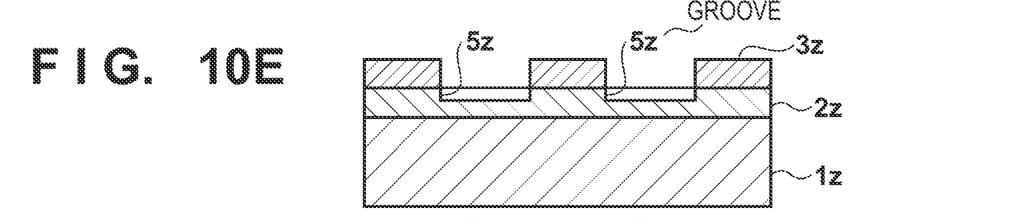
Figure 10F:
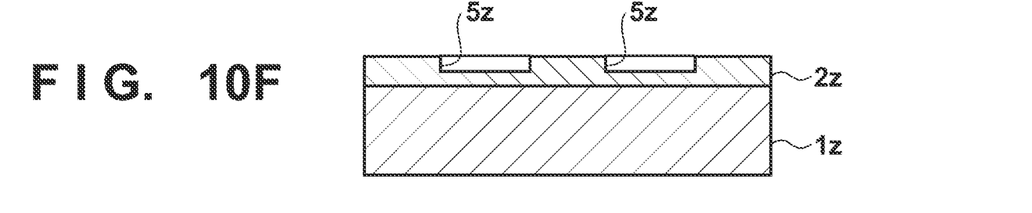

As shown in FIG. 10E, when etching is performed using the pattern of the cured product as an etching resistant mold, a portion of the surface of the processed material 2z where the cured product does not exist or remains thin is removed to form a groove 5z. As shown in FIG. 10F, when the pattern of the cured product is removed, an article with the grooves 5z formed in the surface of the processed material 2z can be obtained. Here, the pattern of the cured product is removed. However, instead of processing or removing the pattern of the cured product, it may be used as, for example, an interlayer dielectric film included in a semiconductor element or the like, that is, a constituent member of an article.

Figure 11A:
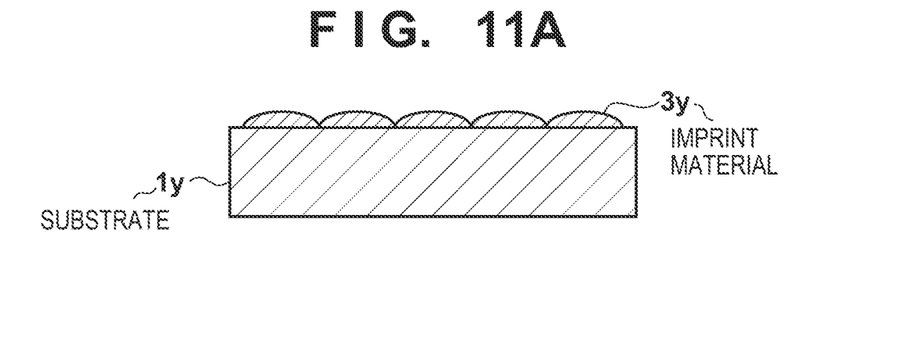
FIGS. 11A to 11D are views showing another example of the method of manufacturing the article.

Another method of manufacturing an article will be described next. As shown in FIG. 11A, a substrate 1y such as silica glass or the like is prepared. Next, an imprint material 3y is applied to the surface of the substrate 1y by an inkjet method or the like. A layer of another material such as a metal or a metallic compound may be provided on the surface of the substrate 1y as needed.

Figure 11B:
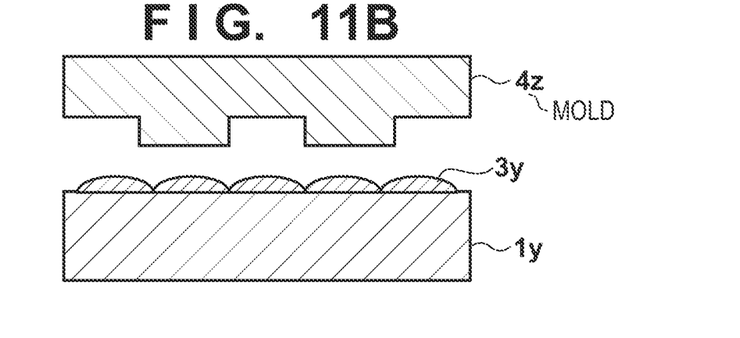
Figure 11C:
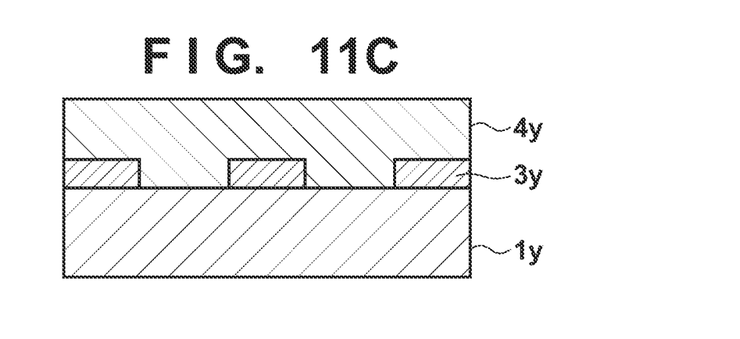

As shown in FIG. 11B, a side of a mold 4y for imprint with an uneven pattern is directed to and caused to face the imprint material 3y on the substrate. As shown in FIG. 11C, the substrate 1y to which the imprint material 3y is applied is brought into contact with the mold 4y, and a pressure is applied. The gap between the mold 4y and the substrate 1y is filled with the imprint material 3y. In this state, when the imprint material 3y is irradiated with light via the mold 4y, the imprint material 3y is cured.

Figure 11D:
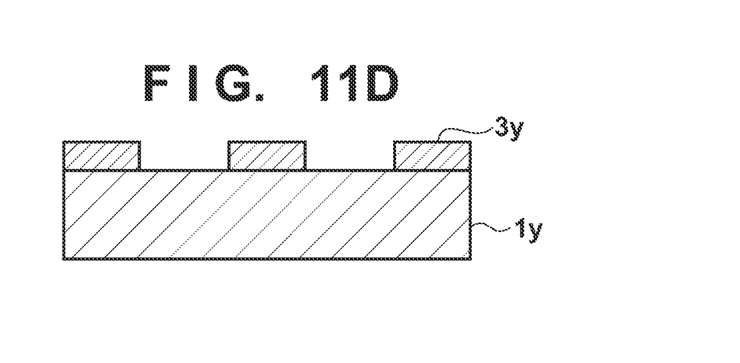

As shown in FIG. 11D, after the imprint material 3y is cured, the mold 4y is separated from the substrate 1y. Then, the pattern of the cured product of the imprint material 3y is formed on the substrate 1y. An article which has the pattern of a cured product as the constituent member is obtained in this manner. Note that if the substrate 1y is etched by using the pattern of the cured product as a mask in the state of FIG.

11D, an article, for example, a mold for imprint, whose concave portions and convex portions have been inverted with respect to the mold 4y can be obtained.

A manufacturing method of manufacturing an article (a semiconductor IC element, a liquid crystal display element, a MEMS, or the like) by performing an exposure process by an exposure apparatus on a substrate inspected by the foreign substance inspection apparatus 1 will be described next. An article is manufactured by performing a process of exposing a substrate (a wafer, a glass substrate, or the like) applied with a photosensitive material by using the exposure apparatus described above, performing a process of developing the substrate (photosensitive material), and processing the developed substrate by other known processes. The other known processes include etching, resist removal, dicing, bonding, packaging, and the like. An article of a higher quality than that of a related art can be manufactured according to this article manufacturing method.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-052919, filed Mar. 20, 2018, which is hereby incorporated by reference herein in its entirety.

What is claimed is:

1. A foreign substance inspection apparatus that performs foreign substance detection processing of detecting a foreign substance present on a surface of a substrate, comprising:
   a detector that includes a projector configured to project light onto the surface and an optical receiver configured to receive scattered light from the surface;
   a scanning mechanism configured to scan a position on the surface onto which the light is projected by the projector; and
   a controller configured to control the foreign substance detection processing so that detection of the foreign substance is performed on a detection region which is a region excluding, from the surface, an exclusion region where a step is present thereon,
   wherein the controller controls the projection by the projector so that light is not projected to the step.

2. The apparatus according to claim 1, wherein the controller generates projection control data for controlling the projection by the projector in accordance with the scanning by the scanning mechanism so the light will be projected to the detection region.

3. The apparatus according to claim 2, further comprising a measurement device configured to measure a state of the substrate,
   wherein the controller generates the projection control data by correcting, based on a measurement result by the measurement device, template data for controlling the projection by the projector.

4. The apparatus according to claim 3, wherein the substrate includes an alignment mark, and
   the measurement device measures the position of the alignment mark.

5. The apparatus according to claim 4, wherein the controller corrects a position of a detected foreign substance based on the measurement result by the measurement device.

6. The apparatus according to claim 4, wherein the controller executes template data generation processing to generate the template data,
   wherein the template data generation processing includes:
   a measurement process of associating a position on the surface of the test substrate with a signal obtained from an output from the optical receiver while causing the scanning mechanism to operate and causing the projector to project light onto a surface of a test substrate, and storing the associated position and the signal; and
   a generation process of generating, based on the signal stored in the measurement process, the template data so the projector will not project light to the step, and
   wherein a sensitivity of the detector in the measurement process is lower than a sensitivity of the detector in the foreign substance detection processing.

7. The apparatus according to claim 6, wherein in the measurement, the controller controls the scanning mechanism so the entire test substrate is scanned.

8. The apparatus according to claim 3, wherein the measurement device measures a height of the surface of the substrate.

9. The apparatus according to claim 3, wherein the measurement device measures errors related to a position and a rotation of the substrate based on an outer shape of the substrate.

10. The apparatus according to claim 1, wherein the scanning mechanism includes a polygon mirror configured to scan the light from the projector, and
    the controller controls the projection of light by the projector in synchronization with the rotation of the polygon mirror.

11. The apparatus according to claim 1, wherein the substrate includes a plurality of regions divided by a scribe line, and
    the step includes a step formed by the scribe line.

12. A processing apparatus that process a substrate, comprising:
    a forming apparatus configure to perform forming processing of forming a composition on the substrate by using a mold; and
    a foreign substance inspection apparatus defined in claim 1 and configured to inspect a foreign substance on a surface of the substrate.

13. A method of manufacturing an article, comprising:
    forming a composition on a substrate by using a processing apparatus defined in claim 12; and
    processing the formed substrate,
    wherein an article is manufactured from the processed substrate.

14. A method of manufacturing an article, comprising:
    detecting a foreign substance present on a surface of a substrate by using a detector that includes a projector configured to project light to the surface of the substrate and an optical receiver configured to receive scattered light from the surface and a scanning mechanism configured to scan the surface by the light from the projector; and controlling the projection by the projector so that light is not projected to an exclusion region of the surface, the exclusion region being a region where a step is present thereon;
    forming a composition on the substrate that has undergone the foreign substance detection; and
    manufacturing an article by processing the substrate that has undergone the forming.

* * * * *